United States Patent
Ip et al.

(10) Patent No.: US 9,134,327 B2
(45) Date of Patent: Sep. 15, 2015

(54) STAT3 AND TYK2 AS DRUG TARGETS FOR NEURODEGENERATIVE DISEASES

(75) Inventors: Nancy Yuk-Yu Ip, Hong Kong (HK); Zhenguo Wu, Kowloon (HK); Jerry Hsueh-Ching Wang, NW Calgary (CA); Kit Yu Fu, Kowloon (HK); Jun Wan, Kowloon (HK)

(73) Assignee: Biotechnology Research Corporation Limited, Kowloon (HK)

( * ) Notice: Subject to any disclaimer, the term of this patent is extended or adjusted under 35 U.S.C. 154(b) by 220 days.

(21) Appl. No.: 13/000,303

(22) PCT Filed: Jun. 30, 2008

(86) PCT No.: PCT/CN2008/001245
§ 371 (c)(1),
(2), (4) Date: Apr. 20, 2011

(87) PCT Pub. No.: WO2010/000089
PCT Pub. Date: Jan. 7, 2010

(65) Prior Publication Data
US 2011/0189681 A1    Aug. 4, 2011

(51) Int. Cl.
*C12Q 1/42* (2006.01)
*A61P 25/28* (2006.01)
*G01N 33/68* (2006.01)

(52) U.S. Cl.
CPC ........ *G01N 33/6896* (2013.01); *G01N 33/6872* (2013.01); *G01N 2333/9121* (2013.01); *G01N 2500/04* (2013.01); *G01N 2500/10* (2013.01); *G01N 2500/20* (2013.01); *Y10T 436/143333* (2015.01)

(58) Field of Classification Search
None
See application file for complete search history.

(56) References Cited

U.S. PATENT DOCUMENTS
2008/0102055 A1    5/2008  Chiba et al.

FOREIGN PATENT DOCUMENTS

| CN | 1733916 A | 2/2006 | |
|---|---|---|---|
| WO | 9841090 A | 9/1998 | |
| WO | WO98/41090 * | 9/1998 | ............. A01N 37/18 |
| WO | 2007/030693 A2 | 3/2007 | |

OTHER PUBLICATIONS

Hashimoto et al., Involvement of tyrosine kinases and STAT3 in Humanin-mediated neuroprotection. Life Sciences 77 (2005) 3092-3104.*
Shen et al., Reduced STAT3 activity in mice mimics clinical disease syndromes. Biochemical and Biophysical Research Communications 330 (2005) 305-309.*
Wen et al., Transcriptional Regulation of b-Secretase by p25/cdk5 Leads to Enhanced Amyloidogenic Processing. Neuron 57, 680-690, Mar. 13, 2008.*
Chinese Office Action with English Translation issued in Application No. 200880130414.9 on Aug. 28, 2012, 17 pages.
(Continued)

*Primary Examiner* — Gregory S Emch
*Assistant Examiner* — Aurora M Fontainhas
(74) *Attorney, Agent, or Firm* — Kilpatrick Townsend & Stockton LLP (57) ABSTRACT

The invention provides Stat3 and Tyk2 targets that have importance for diagnosis of neurodegenerative diseases such as Alzheimer's disease. Stat3 and Tyk2 are also important as targets for drug development for neurodegenerative diseases.

11 Claims, 5 Drawing Sheets

(56) References Cited

OTHER PUBLICATIONS

Jrawan Satnotomo et al, "JAK2 and STAT3 activation contributes to neuronal damage following transient focal cerebral ischemia", Journal of Neurochemistry, Sep. 1, 2006, vol. 98, pp. 1353-1368.

Ana M. Gamero et al., "Activation of Tyk2 and Stat3 is required for the apoptotic actions of Interferon-B in primary pro-B cells", Journal of Biological Chemistry, Jun. 16, 2006, vol. 281 No. 24, pp. 16238-16244.

First UK Office Action Issued in Application No. GB 1100021.3 on Dec. 29, 2011, 5 pages.

Second UK Office Action Issued in Application No. GB1100021.3 on Jul. 2, 2012, 4 pages.

\* cited by examiner

STAT3 AND TYK2 AS DRUG TARGETS FOR NEURODEGENERATIVE DISEASES

BACKGROUND OF THE INVENTION

Neurodegenerative diseases such as Alzheimer's Disease (AD) mainly affect the elderly. AD is a progressive disease which results in cognitive decline and dementia. Two pathological hallmarks of AD are intracellular neurofibrillary tangles (NFTs) and extracellular senile plaques (NPs). The former accumulates inside dying cells while the latter builds up between nerve cells. Various processes have been implicated in neurodegenerative pathogenesis, including β-amyloid production, hyperphosphorylation of tau, oxidative stress, inflammation, synaptic failure and neuronal apoptosis. The actual cause of AD, however, remains elusive. One hypothesis states that neuronal loss in AD is due to the accumulation of toxic protein. β-amyloid is a cleavage product derived from amyloid precursor protein (APP), which accumulates as extracellular plaque in AD brain. Emerging studies reveal that deregulation of specific intracellular signaling pathways results in AD or Aβ-induced neuronal apoptosis. For example, activation of JNK and p38 was found to associate with the AD mice model (Savage et al. (2002) *J Neurosci* 22:3376-85). The glycogen synthase kinase (GSK)-3 pathway has also been shown to be involved in oxidative stress-induced neuronal cell death mechanisms (Koh et al. (2003) *Brain Res Mol Brain Res* 118:72-81; Takadera et al. (2004) *Eur J Pharmacol.* 499:239-45). Furthermore, inhibition of GSK-3 reduces Aβ-induced neurotoxicity (Koh et al. (2008) *Brain Res* 1188:254-62). Similarly, both Wnt and Notch signaling play roles in the pathogenesis of AD (De Strooper et al. (2001) *J Cell Biol* 152:F17-20; Anderton et al., (2000) *Mol Med Today* 6:54-9).

Currently, the clinical diagnosis of AD requires an evaluation of medical history and physical examination including neurological, neuropsychological and psychiatric assessment, as well as various biological, radiological and electrophysiological tests. Despite the battery of tests, a definitive diagnosis can only be achieved by post-mortem brain examination.

There is therefore an unmet need for a simple biochemical test that can detect neurodegeneration at an early stage and monitor progression of related diseases and disorders. Aging populations in, for example, the U.S., Europe, and China are increasingly seeking improved diagnostic and therapeutic tools for AD and other neurodegenerative disorders.

The invention relates to the association of another signal pathway to AD pathology and the identification of two novel targets involved in the molecular mechanism of AD, namely, STAT3 protein and TYK2, the upstream regulator of STAT3. STAT3 and TYK2 have major implications in the diagnosis of AD as well as in the development of therapeutic drugs against the disease. Previously, STAT3 over-expression has only been associated with inflammation and cancer.

STAT3 and its upstream regulator TYK2 both play key roles in Aβ-induced neural cytotoxicity. STAT3 phosphorylation at tyrosine 705 is elevated in the cortex and hippocampi of AD brains, which can promote apoptosis of cortical neurons, while TYK2 mediates STAT3 phosphorylation and activation. Blocking one or both of these targets can prevent Aβ-induced cell death and could potentially halt disease progression. Thus, the invention has major significance in developing drugs in the treatment of AD, as well as in the diagnosis of the disease.

BRIEF SUMMARY OF THE INVENTION

In some embodiments, the invention provides methods and compositions to identify compounds that modulate neurodegenerative disorders, e.g., Alzheimer's Disease (AD). In some embodiments, the method comprises the steps of (i) contacting a compound with a STAT3 or TYK2 polypeptide; and (ii) determining the functional effect of the compound on STAT3 or TYK2, wherein a functional effect indicates that the compound modulates a neurodegenerative disorder. In some embodiments, the method comprises the steps of (i) contacting a compound with a polynucleotide encoding a STAT3 or TYK2 polypeptide; and (ii) determining the functional effect of the compound on STAT3 or TYK2, wherein a functional effect indicates that the compound modulates a neurodegenerative disorder. One of skill in the art will appreciate that such methods include controls, e.g., to ascertain STAT3 and TYK2 expression or activity in the absence of the compound, or in the presence of a known activator compound.

In some embodiments, the neurological disorder is characterized by deposits of amyloid peptides in the brain, e.g., Alzheimer's Disease (AD). In some embodiments, the neurological disorder is selected from the group consisting of: AD, mild cognitive impairment, Parkinson's disease, Dentatorubro-pallidoluysian Atrophy (DRPLA), Neuronal Intranuclear Hyaline Inclusion Disease (NIHID), dementia with Lewy bodies, Down's Syndrome, Hallervorden-Spatz disease, prion diseases, argyrophilic grain dementia, cortocobasal degeneration, dementia pugilistica, diffuse neurofibrillary tangles, Gerstmann-Straussler-Scheinker disease, Hallervorden-Spatz disease, Jakob-Creutzfeldt disease, Niemann-Pick disease type 3, progressive supranuclear palsy, subacute sclerosing panencephalitis, Spinocerebellar Ataxias, Huntington's disease, Pick's disease, and dentatorubral-pallidoluysian atrophy.

In some embodiments, the polynucleotide or polypeptide is recombinant. In some embodiments, the functional effect is determined in vitro. In some embodiments, the functional effect is determined in a eukaryotic cell, such as a neuronal cell.

In some embodiments, the functional effect is determined by measuring the expression of TYK2 or STAT3. In some embodiments, the expression is determined using a hybridization-based assay, e.g., RT-PCR. Alternatively, the expression is determined using a protein-based assay, e.g., an immunoassay.

In some embodiments, the functional effect is determined by measuring the phosphorylation or kinase activity of TYK2. In some embodiments, the functional effect is determined by measuring phosphorylation of STAT3, e.g., at tyrosine 705. In some embodiments, the functional effect is determined by measuring STAT3 activity, e.g., dimerization or downstream transcriptional activation. In some embodiments, the functional effect is determined by measuring apoptosis of the cell.

In some embodiments, the compound is selected from an antisense molecule, an RNAi molecule, an antibody or antibody fragment, a small peptide, or a small organic molecule specific for TYK2 or STAT3.

The invention also provides methods and compositions for diagnosing neurodegenerative disorders and diseases. In some embodiments, the method comprises the steps of: (i) obtaining a biological sample from an individual; (ii) determining the level of TYK2 polynucleotide or polypeptide in the sample; and (iii) comparing the level of TYK2 in the sample from step (ii) to the level of TYK2 in a normal biological sample, thereby diagnosing a neurodegenerative disorder in the individual.

In some embodiments, the determining step comprises a hybridization-based assay, such as RT-PCR, or a protein-based assay, such as an immunoassay. In some embodiments, the determining step comprises a functional assay, such as a kinase assay. In some embodiments, the level of phosphorylated Tyk2 is determined and compared.

In some embodiments, the method comprises the steps of: (i) obtaining a biological sample from the individual; (ii) determining the level of STAT3 polynucleotide or polypeptide in the sample; and (iii) comparing the level of STAT3 in the sample from step (ii) to the level of STAT3 in a normal biological sample, thereby diagnosing a neurodegenerative disorder in the individual.

In some embodiments, the determining step comprises a hybridization-based assay, such as RT-PCR, or a protein-based assay, such as an immunoassay. In some embodiments, the determining step comprises a functional assay, e.g., to measure STAT3-dependent gene expression. In some embodiments, the level of phosphorylated STAT3 polypeptide is determined, e.g., STAT3 phosphorylation on tyrosine 705.

In some embodiments, the neurodegenerative disorder is characterized by deposits of amyloid peptides in the brain, e.g., AD. In some embodiments, the neurodegenerative disorder is selected from the group consisting of: Alzheimer's Disease (AD), mild cognitive impairment, Parkinson's disease, Dentatorubro-pallidoluysian Atrophy (DRPLA), Neuronal Intranuclear Hyaline Inclusion Disease (NIHID), dementia with Lewy bodies, Down's Syndrome, Hallervorden-Spatz disease, prion diseases, argyrophilic grain dementia, cortocobasal degeneration, dementia pugilistica, diffuse neurofibrillary tangles, Gerstmann-Straussler-Scheinker disease, Hallervorden-Spatz disease, Jakob-Creutzfeldt disease, Niemann-Pick disease type 3, progressive supranuclear palsy, subacute sclerosing panencephalitis, Spinocerebellar Ataxias, Huntington's disease, Pick's disease, and dentatorubral-pallidoluysian atrophy.

In some embodiments, a level of TYK2 or STAT3 expression or activity that is increased over the normal sample indicates a neurodegenerative disorder in the individual. In some embodiments, the method is used in combination with other diagnostic methods, as described herein.

BRIEF DESCRIPTION OF THE DRAWINGS

FIG. 3: Knockdown of STAT3 protects neurons from Aβ-induced apoptosis. A. Knockdown of STAT3 reduced cell death of PC12 cells induced by Aβ25-35 treatment. PC12 cells were transfected with STAT3 siRNA. Western blot analysis for STAT3 confirmed the knockdown of STAT3 in PC12 cells transfected with STAT3 siRNA but not the scramble siRNA for 3 days (α-tubulin serves as a loading control). The PC12 cells transfected with STAT3 siRNA for 3 days were treated with Aβ25-35 for 24 hr. Cell viability was assessed by the MTT assay *, p<0.05. B. Blocking STAT3 activation attenuated the increase of cleaved caspase-3 in neurons after treatment with Aβ25-35. Cortical neurons were pretreated with cell-permeable STAT3 inhibitor peptide (200 μg/ml) for 30 minutes prior to the Aβ25-35 treatment. The cell lysates were then analysed by immunoblotting using caspase-3 antibody. The cleaved caspase-3 level was quantified.

FIG. 4: Tyk2 is required for beta-amyloid peptide-induced tyrosine phosphorylation of STAT3 and neuronal cell death. A. Primary cortical neurons were pretreated with various inhibitors including a potent inhibitor of JAK (JAK inhibitor 1), a JAK2 inhibitor (AG490), a Src tyrosine kinase inhibitor (PP2) and a protein synthesis inhibitor (cycloheximide) for 2 hrs as indicated, followed by treatment with Aβ25-35 peptide for 4 hrs or 24 rs. The cell lysates were immunoblotted with P-Tyr STAT3 and total STAT3 antibody. B. Primary cortical neurons were treated with Aβ25-35. The cell lysates were immunoprecipitated using Tyk2 or JAK2 antibody, and then subjected to Western blot analysis for phospho-tyrosine (P-Tyr) antibody. C. Primary cortical neurons prepared from $Tyk2^{-/-}$ mice were treated with Aβ25-35. The cell lysates were subjected to immunoblotting using P-Tyr STAT3, total STAT3 and caspase-3 antibody. Quantification analysis of fold change in tyrosine phosphorylated STAT3 and cleaved caspase-3 (bottom panels).

FIG. 5: Transcription activity of STAT3 in PC12 cells and iNOS RNA in cultured cortical neurons increases upon stimulation with Aβ25-35. A. PC12 cells were transfected with a STAT1 (pGAS-Luc) or STAT3 (pSTAT3-Luc) reporter gene construct together with an internal control plasmid (β-galactosidase-pCMV). The cells were differentiated by NGF for 4 days, and were then treated with Aβ25-35 or NGF (positive control) for 1 day. Luciferase activity was measured and normalized against the β-galactosidase activity in the samples. Results were normalized with β-galactosidase activity; mean±S.E., n=3; *, p<0.05. B. Primary cortical neurons at 7 DIV were pretreated with STAT3 inhibitor or JAK inhibitor I for 30 minutes, followed by Aβ25-35 (40 μM) treatment for 6 hours. Total RNA was collected and subjected to reverse transcription. The cDNA was then subjected to real-time PCR analysis using iNOS primers.

DETAILED DESCRIPTION OF THE INVENTION

The current invention establishes a link between elevated STAT3 phosphorylation and neurodegerative disorders, such as Alzheimer's Disease (AD). We have found that amyloid beta (Aβ), a hallmark of AD, induces activation of STAT3 and that STAT3 activation is required for neuronal apoptosis. TYK2 is the upstream regulator that mediates the Aβ induced tyrosine phosphorylation of STAT3 in AD.

As demonstrated in the Examples below, tyrosine phosphorylation of STAT3 is consistently elevated in the cortex and hippocampus of the brains of a number of mouse models exhibiting AD pathology. Active STAT3 (i.e., STAT3 phosphorylated at tyrosine 705) is also detected in brain regions with senile plaques, which are deposits of Aβ. In contrast, tyrosine phosphorylation of STAT3 is barely detected in the cortex of wild-type mice, thus suggesting a link between elevated pTyr-STAT3 levels and AD pathology.

Another correlation of the STAT3 to AD is the link between STAT3 phosphorylated at tyrosine 705 and Aβ. Aβ is found to induce phosphorylation and activation of STAT3 which results in neuronal cell death. Furthermore, when STAT3 activation is blocked, there is a significant reduction in cell death induced by Aβ, suggesting that STAT3 activity plays a key role in Aβ-induced neuronal cell death.

The invention also includes a newly recognized role for TYK2 in AD pathology, as it mediates Aβ-induced tyrosine phosphorylation of STAT3. In cortical neurons derived from TYK2 knock-out mice, Aβ-induced phosphorylation of STAT3 at tyrosine 705 is attenuated. Hence, our accumulated findings identify STAT3 and TYK2 as core targets for drug development for neurodegenerative disorders, as well as for diagnosis.

A. DEFINITIONS

As used herein, "STAT3" refers to a member of the signal transducer and activator of transcription (STAT) protein family. STAT3 has two splice variants named STAT3α (p92) and β (p83). An example of a STAT3 polypeptide is the human STAT3 polypeptide described in Genbank accession number P40763.2, which contains a tyrosine at amino acid 705. An exemplary STAT3 coding sequence is the human sequence described in Genbank accession number L29277. STAT3 also refers to species homologs, splice variants, polymorphic variants, and conservatively modified variants of STAT3 that possess STAT3 signaling activity.

As used herein, "TYK2" refers to a member of the Janus Kinase (JAK) family of tyrosine kinases. An example of TYK2 polypeptide is the human polypeptide sequence described in Genbank accession number P29597.3. An exemplary TYK2 coding sequence is the human sequence described in Genbank accession number X54637. TYK2 also includes species homologs, splice variants, polymorphic variants, and conservatively modified variants of TYK2 that retain TYK2 tyrosine kinase activity.

The terms "neurodegenerative disease" and "neurodegenerative disorder," used interchangeably herein, refer to disorders that include Alzheimer's Disease (AD), Parkinson's disease, Dentatorubro-pallidoluysian Atrophy (DRPLA), Neuronal Intranuclear Hyaline Inclusion Disease (NIHID), dementia with Lewy bodies, Down's Syndrome, Hallervorden-Spatz disease, prion diseases, argyrophilic grain dementia, cortocobasal degeneration, dementia pugilistica, diffuse neurofibrillary tangles, Gerstmann-Straussler-Scheinker disease, Hallervorden-Spatz disease, Jakob-Creutzfeldt disease, Niemann-Pick disease type 3, progressive supranuclear palsy, subacute sclerosing panencephalitis, Spinocerebellar Ataxias, Huntington's disease, Pick's disease, and dentatorubral-pallidoluysian atrophy. Neurodegenerative disorders are often characterized by neurofibrillary tangles and/or deposits of amyloid peptides in the brain.

"Diagnosis" of a neurodegenerative disease or disorder refers to a prediction of symptoms related to these disorders, e.g., impaired cognitive function, accumulated Aβ deposits, and neuronal cell death. In some embodiments, cognitive function can be measured by Mini-Mental State Exam in accordance with convention. In one embodiment, the prognosis may be used to tailor a therapy to provide a better outcome.

"Biological sample" includes sections of tissues such as a biopsy sample (e.g., a neuronal biopsy) or a frozen section taken for histologic purposes. Such samples also include blood and blood fractions (e.g., serum, platelets, red blood cells, and the like), cerebrospinal fluid, cultured cells, e.g., primary cultures, explants, and transformed cells, stool, urine, etc. A biological sample is typically obtained from a mammal, e.g., a primate or human.

As used herein, a "normal biological sample" or "normal individual" represents a baseline value, or control. "Normal" is representative of levels of the polynucleotide or nucleic acid in a healthy person not suffering from, or destined to develop, a neurodegenerative disorder, as determined using standard methods, e.g., a cognitive test or with a biological sample (e.g., a neuronal biopsy or cerebrospinal fluid).

A "nucleic acid," "nucleotide," or "polynucleotide" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The terms "overexpress," "overexpression" or "overexpressed" interchangeably refer to a protein or nucleic acid (RNA) that is transcribed or translated at a detectably greater level in a cell in comparison to a normal cell. The term includes overexpression due to transcription, post transcriptional processing, translation, post-translational processing, cellular localization (e.g., organelle, cytoplasm, nucleus, cell surface), and RNA and protein stability, as compared to a normal cell. Overexpression can be detected using conventional techniques for detecting mRNA (i.e., RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold, or much higher level of transcription or translation in comparison to a normal cell.

The terms "underexpress," "underexpression" or "underexpressed" or "downregulated" interchangeably refer to a protein or nucleic acid that is transcribed or translated at a detectably lower level in a cell in comparison to a normal cell. The term includes underexpression due to transcription, post transcriptional processing, translation, post-translational processing, cellular localization (e.g., organelle, cytoplasm, nucleus, cell surface), and RNA and protein stability, as compared to a control. Underexpression can be detected using conventional techniques for detecting mRNA (i.e., RT-PCR, PCR, hybridization) or proteins (i.e., ELISA, immunohistochemical techniques). Underexpression can be 10%, 20%, 30%, 40%, 50%, 60%, 70%, 80%, 90% or less in comparison to a control. In certain instances, underexpression is 1-fold, 2-fold, 3-fold, 4-fold or more lower levels of transcription or translation in comparison to a control.

The term "differentially expressed" or "differentially regulated" refers generally to a protein or nucleic acid that is overexpressed (upregulated) or underexpressed (downregulated) in one sample compared to at least one other sample. For the purposes of the invention, a sample from an individual suspected of having a neurodegenerative disorder is generally compared to a sample from an individual that is known to have the disorder (positive control) or one that is known to be negative for the disorder (negative control).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide. Labels can be attached to targeting molecules such as antibodies or nucleotide sequences for specific detection of a targeted compound.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

As used herein, the term "single-chain antibody" (scFv) refers to a polypeptide comprising a VH domain and a VL domain in polypeptide linkage, generally linked via a spacer peptide (e.g., [Gly-Gly-Gly-Gly-Ser]$_x$), and which may comprise additional amino acid sequences at the amino- and/or carboxyl-termini. For example, a single-chain antibody may comprise a tether segment for linking to the encoding polynucleotide. As an example, a scFv is a single-chain antibody. Single-chain antibodies are generally proteins consisting of one or more polypeptide segments of at least 10 contiguous amino acids substantially encoded by genes of the immunoglobulin superfamily (e.g., see The Immunoglobulin Gene Superfamily, A. F. Williams and A. N. Barclay, in Immunoglobulin Genes, T. Honjo, F. W. Alt, and T. H. Rabbitts, eds., (1989) Academic Press: San Diego, Calif., pp. 361-387, which is incorporated herein by reference), most frequently encoded by a rodent, non-human primate, avian, porcine, bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

As used herein "antibody" may also refer to any functional VH and VL pair (i.e., capable of binding specifically to an epitope) that are each linked in various configurations to other polypeptide(s) that may perform various functions, e.g., as reporter, reporter inhibitor, or stabilizer of the VH-VL complex.

As used herein "immunoglobulin variable region domain" refers to any VH or VL domain used as a binding moiety without a companion VH or VL domain. As with antibodies, such domains may be linked in various configurations to other polypeptide(s) that may perform various functions, e.g., as reporter, reporter inhibitor, or reporter activator.

The phrase "specifically (or selectively) binds" when referring to a protein, nucleic acid, antibody, or small molecule compound refers to a binding reaction that is determinative of the presence of the protein or nucleic acid (e.g., STAT3, TYK2, or modified versions thereof), often in a heterogeneous population of proteins or nucleic acids and other biologics. In the case of antibodies, under designated immunoassay conditions, a specified antibody may bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

The phrase "functional effects", in the context of assays for testing compounds that modulate AD or an neurodegeneration biomarker, includes the determination of a parameter that is indirectly or directly under the influence of a biomarker of the invention, e.g., a chemical or phenotypic effect. A functional effect therefore includes immediate signaling events, such as transcriptional activation or phosphorylation, or more indirect effects, such as gene expression or apoptosis of the cell. "Functional effects" include in vitro, in vivo, and ex vivo activities.

By "determining the functional effect" is meant assaying for a compound that increases or decreases a parameter that is indirectly or directly under the influence of a biomarker of the invention, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape), chromatographic; or solubility properties for the protein; measuring inducible markers or transcriptional activation of the marker; measuring changes in enzymatic (e.g., kinase) activity; the ability to increase or decrease cellular proliferation, apoptosis, cell cycle arrest, measuring changes in cell surface markers. The functional effects can be evaluated by many means known to those skilled in the art, e.g., microscopy for quantitative or qualitative measures of alterations in morphological features, measurement of changes in RNA or protein levels for other genes expressed in the cell, measurement of RNA stability, identification of downstream or reporter gene expression (CAT, luciferase, β-gal, GFP and the like), e.g., via chemiluminescence, fluorescence, colorimetric reactions, antibody binding, inducible markers, etc.

"Activity" of a neurodegeneration biomarker polypeptide refers to structural, regulatory, or biochemical functions of the polypeptide in its native cell or tissue. Activities of neurodegeneration biomarkers include both direct activities and indirect activities. An exemplary direct activity is catalytic activity, i.e., kinase activity for TYK2. Direct activities of phosphorylated STAT3 include dimerization and transcriptional activation. Exemplary indirect activities are observed as a change in phenotype or response in a cell or tissue to a polypeptide's direct activity, e.g., apoptosis. Catalytic activity can be measured, e.g., by determining the amount of a substrate that is phosphorylated. Other activities, e.g., apoptosis, may also be assessed using methods known in the art.

"Inhibitors," "activators," and "modulators" of the markers are used to refer to activating, inhibitory, or modulating molecules identified using in vitro and in vivo assays of neurodegeneration biomarkers (e.g., STAT3, TYK2, phosphorylated STAT3, phosphorylated TYK2). Inhibitors are compounds that, e.g., bind to, partially or totally block activity, decrease, prevent, delay activation, inactivate, desensitize, or down regulate the activity or expression of neurodegeneration biomarkers. "Activators" are compounds that increase, open, activate, facilitate, enhance activation, sensitize, agonize, or up-regulate activity of neurodegeneration biomarkers, e.g., agonists. Inhibitors, activators, or modulators also include genetically modified versions of neurodegeneration biomarkers, e.g., versions with altered activity, as well as naturally occurring and synthetic ligands, antagonists, agonists, antibodies, peptides, cyclic peptides, nucleic acids, antisense molecules, ribozymes, RNAi and siRNA molecules, small organic molecules and the like. Such assays for inhibitors and activators include, e.g., expressing neurodegeneration biomarkers in vitro, in cells, or cell extracts, applying putative modulator compounds, and then determining the functional effects on activity, as described above.

Samples or assays comprising neurodegeneration biomarkers (e.g., TYK2, STAT3, phosphorylated STAT3, phosphorylated TYK2) that are treated with a potential activator, inhibitor, or modulator are compared to control samples without the inhibitor, activator, or modulator to examine the extent of activity change. Control samples (untreated or, alternatively, treated with a known modulator) are assigned a relative protein activity value of 100%. Inhibition of neurodegeneration biomarkers is achieved when the activity value relative to the control is about 80%, preferably 50%, more preferably 25-0%. Activation of neurodegeneration biomarkers is achieved when the activity value relative to the control (untreated with activators) is 110%, more preferably 150%, more preferably 200-500% (i.e., two to five fold higher relative to the control), more preferably 1000-3000% higher.

The term "test compound," "test agent," "modulator," or equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, peptide, circular peptide, lipid, fatty acid, siRNA, polynucleotide, oligonucleotide, etc., to be tested for the capacity to directly or indirectly modulate neurodegeneration biomarkers. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

The terms "small organic molecule" and "small molecule" refer to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

B. STAT3 AND TYK2

STAT3 belongs to the family of signal transducer and activator of transcription (STAT) proteins. Like other members of this family, it is activated by phosphorylation via receptor-associated kinases. Once phosphorylated, STAT proteins then form homo- or heterodimers that translocate to the cell nucleus where they act as transcriptional activators. In addition to the tyrosine phosphorylation required for both dimerization and translocation to the nucleus, STAT proteins also require serine phosphorylation for optimal transcriptional activation (Zhang et al. (1995) Science 267:1990-94).

STAT3 is activated in response to stimulation by growth factors (e.g., epidermal growth factor, CSF-1, and PDGF), and various interferons and cytokines (e.g., IFNα, IL-6, LIF) (Akira (2000) Oncogene 19:2607-11). STAT3 activation via IL-6 family of cytokines results in various functional responses. Upon stimulation, the cytokine binds to gp130 and other related receptors to trigger STAT3 phosphorylation by a Janus kinase (JAKs). Phosphorylation occurs upon a single tyrosine site at amino acid 705 within the transactivation domain, resulting in STAT3 dimerization, translocation and DNA binding (Levy and Lee (2002) J Clin Invest 109:1143-48).

As it is activated in response to a large number of signaling molecules and mediates a range of different signal pathways, STAT3 functions are versatile (i.e. its actions can lead to proliferation, promote survival or cause apoptosis). Based on numerous published reports, its functionality includes the induction of an acute phase response in hepatoma cells (Alonzi et al. (2001) Mol Cell Biol 21:1621-32), stimulation of B lymphocyte proliferation, activation of monocyte differentiation and growth arrest (Heinrich et al. (1998) Biochem J 334:297-314), maintenance of the pluripotency of embryonic stem cells (Raz et al. (1999) Proc Natl Acad Sci USA 96:2846-51), as well as a role in liver regeneration (Moh et al. (2007) Lab Invest 87:1018-28). The transcriptional activity of STAT3 has also been found to be important in neuronal survival (Battle and Frank (2002) Curr Mol Med 2:381-92).

Tyk2 belongs to the JAK family of intracellular protein-tyrosine kinases (PTKs), which includes JAK1, JAK2, and JAK3. These PTKs have two tandemly arranged kinase domains: a carboxyl-terminal, functional tyrosine kinase (TK) domain and an adjacent kinase-like (KL) domain. The JAKs play a crucial role in signaling through a number of cellular receptors, as was first demonstrated by their ability to complement the genetic defect of mutant cell lines unresponsive to interferons (IFN). It was later found that ligand binding to almost all known cytokine receptors induces the tyrosine phosphorylation of one or more JAK family members. These PTKs phosphorylate downstream effector molecules and are crucial for proper ligand-receptor signaling.

C. GENERAL RECOMBINANT METHODS

To express a cloned gene, such as a cDNA encoding STAT3 or TYK2, one typically subclones the coding sequence into an expression vector that contains a promoter to direct transcription, a transcription/translation terminator, and a ribosome binding site for translational initiation. Suitable bacterial promoters are well known in the art and described, e.g., in Sambrook et al., and Ausubel et al., supra. Bacterial expression systems for expressing the CMR1 protein are available in, e.g., E. coli, Bacillus sp., and Salmonella (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available. Retroviral expression systems can also be used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the STAT3 or TYK2-encoding nucleic acid in host cells. A typical expression cassette thus contains a promoter operably linked to the coding sequence and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

Standard transfection methods are used to produce bacterial, mammalian, yeast or insect cell lines that express a selected protein, which can then be purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell.

After the expression vector is introduced into the cells, the transfected cells are cultured under conditions favoring expression of the selected protein (e.g., TYK2 or STAT3).

D. DIAGNOSTIC METHODS

The present invention provides methods of predicting, diagnosing, or providing a prognosis for a neurodegenerative disorder such as AD by detecting the expression or activation of STAT3 and TYK2. Prediction and prognosis involve determining the level of neurodegeneration biomarker expression or activation in a biological sample from an individual and then comparing the level to a control baseline or range. Typically, the baseline value is representative of levels of the polynucleotide or nucleic acid in a healthy person not suffering from, or destined to develop, a neurodegenerative disorder, as measured using a biological sample such as a neuronal biopsy or a sample of a bodily fluid such as cerebrospinal fluid. Variation of levels of neurodegeneration biomarker expression or activation can indicate that the patient has an increased risk of neurodegeneration. Such methods can be used in combination with other diagnostic methods known in the art.

1. Nucleotide-Based Assays

In some embodiments, real time or quantitative PCR is used to examine expression of STAT3 or TYK2 using RNA from a biological sample. RNA extraction can be performed by any method know to those of skill in the art, e.g., using Trizol and RNeasy. Real time PCR can be performed by any method known to those of skill in the art, e.g., Taqman real time PCR using Applied Biosystem assays. Gene expression is calculated relative to pooled normal lung RNA, and expression is normalized to housekeeping genes. Suitable oligonucleotide primers are selected by those of skill in the art.

In one embodiment, RNA biomarkers are examined using nucleic acid binding molecules such as probes, oligonucleotides, oligonucleotide arrays, and primers to detect differential RNA expression in patient samples. In one embodiment, RT-PCR is used according to standard methods known in the art. In another embodiment; quantitative PCR assays such as Taqman® assays available from, e.g., Applied Biosystems, can be used to detect nucleic acids and variants thereof. In other embodiments, nucleic acid microarrays can be used to detect nucleic acids. Analysis of nucleic acids can be achieved using routine techniques such as northern analysis, or any other methods based on hybridization to a nucleic acid sequence that is complementary to a portion of the marker coding sequence (e.g., slot blot hybridization) are also within the scope of the present invention. Reagents that bind to selected nucleic acid biomarkers can be prepared according to methods known to those of skill in the art or purchased commercially.

Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression From Experiments to Data Analysis and Modeling," Cambridge University Press, 2002.

2. Protein-Based Assays and Immunoassays

In another embodiment, antibody reagents can be used in assays to detect expression and/or activity levels of neurodegeneration biomarkers of the invention in biological samples using any of a number of immunoassays known to those skilled in the art. Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., *Curr. Opin. Biotechnol.,* 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence. See, e.g., Schmalzing et al., *Electrophoresis,* 18:2184-93 (1997); Bao, *J. Chromatogr. B. Biomed. Sci.,* 699:463-80 (1997). Liposome immunoassays, such as flow-injection liposome immunoassays and liposome immunosensors, are also suitable for use in the present invention. See, e.g., Rongen et al., *J. Immunol. Methods,* 204:105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., *J. Clin. Chem. Clin. Biochem.,* 27:261-276 (1989)).

A detectable moiety can be used in the assays described herein for direct or indirect detection. A wide variety of detectable moieties can be used, with the choice of label depending on the sensitivity required, ease of conjugation with the antibody, stability requirements, and available instrumentation and disposal provisions. Suitable detectable moieties include, but are not limited to, radionucleotides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, metals, and the like.

A chemiluminescence assay using a chemiluminescent antibody specific for the nucleic acid is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine. Indirect labels include various enzymes well known in the art, such as horseradish peroxidase (HRP), alkaline phosphatase (Aβ), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Useful physical formats comprise surfaces having a plurality of discrete, addressable locations for the detection of a plurality of different markers. Such formats include microarrays and certain capillary devices. See, e.g., Ng et al., *J. Cell Mol. Med.,* 6:329-340 (2002); U.S. Pat. No. 6,019,944. In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

Analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

Alternatively, the antibodies or nucleic acid probes of the invention can be applied to sections of patient biopsies immobilized on microscope slides. The resulting antibody staining or in situ hybridization pattern can be visualized using any one of a variety of light or fluorescent microscopic methods known in the art.

In another format, the various markers of the invention also provide reagents for in vivo imaging such as, for instance, the imaging of labeled regents that detect the nucleic acids or encoded proteins of the biomarkers of the invention.

Non-invasive medical imaging techniques such as Positron Emisson Tomography (PET) or single photon emission computerized tomography (SPECT) imaging are particularly useful for the detection of brain disease. PET and SPECT imaging shows the chemical functioning of organs and tissues, while other imaging techniques, such as X-ray, CT and MRI, show structure. The use of PET and SPECT imaging has become increasingly useful for qualifying and monitoring the development of brain diseases such as AD. In some instances, the use of PET or SPECT imaging allows a neurodegenerative disorder to be detected several years earlier than the onset of symptoms.

This strategy has been used to develop compounds suitable for in vivo imaging of amyloid deposits in human brains. Monoclonal antibodies against Aβ and peptide fragments have had limited uptake by the brain when tested in patients with AD. The small molecular approach for amyloid imaging has so far been most successful, as described by, e.g., Nordberg A, Lancet Neurol., 3(9):519-27 (2004); Kung M P et al, Brain Res., 1025(1-2):98-105 (2004); Herholz K et al., Mol Imaging Biol., 6(4):239-69 (2004); Neuropsychol Rev., Zakzanis K K et al., 13:1-18 (2003); Herholz K, Ann Nucl Med., 17:79-89 (2003).

The diagnostic compounds disclosed herein, or fragments thereof, can be used in the context of PET and SPECT imaging applications. After modification with appropriate tracer residues for PET or SPECT applications, diagnostic compounds such as antibody fragments, which interact with neurodegeneration biomarker proteins, can be used to image the level of these biomarkers in an individual. Such detection is indicative of the location neurotoxic amyloid deposits characteristic of AD brains.

3. Functional Assays

The expression or activity of neurodegeneration biomarkers can also be detected using functional assays. Such assays will be apparent to one of skill in the art given the known activities of TYK2 (e.g., tyrosine kinase) and STAT3 (dimerization, transcriptional activation), as well as those revealed herein. Assays for detecting the activities of neurodegeneration biomarkers are discussed in more detail in the following sections.

4. Additional Diagnostic Methods

Methods for diagnosing neurodegenerative disorders are known in the art (see, e.g., Diagnostic and Statistical Manual of Mental Disorders, Fourth Edition (DSM-IV-TR), American Psychiatric Assoc. 2000). Generally, a physician or neurologist will consider a number of factors in making a diagnosis in a particular individual or patient. For example, family history is often indicative of a risk of AD and other neurodegenerative disorders. Doctors will also carry out chemical tests to check for normal blood count, thyroid function, liver function, glucose levels. Spinal fluid is often analyzed as part of this testing.

A physician can also used neuropsychological tests to assess memory, problem-solving, attention, vision-motor coordination and abstract thinking. These include spatial exercises and simple calculations. The Mini-Mental State Examination is also common.

CAT scans and MRIs can also be used to rule out tumors, and can provide clues as to degraded areas of the brain.

E. STAT3 AND TYK2 MODULATOR COMPOUNDS

The agents tested as modulators of neurodegeneration biomarkers can be any small chemical compound, or a biological entity, such as a protein, sugar, nucleic acid or lipid. Typically, test compounds will be small chemical molecules, peptides, oligonucleotides, or antibody fragments.

1. Antibodies and Antibody Fragments

In some embodiments, antibodies or epitope-binding fragments thereof can be used to inhibit STAT3 and TYK2 activity. Several antibodies specific for these proteins are known in the art and commercially available (see, e.g., Invitrogen Catalog, available on the World Wide Web at invitrogen.com and BD Biosciences Catalog, available on the World Wide Web at bdbiosciences.com).

Alternatively, a TYK2 or STAT3 antibody can be created de novo using standard techniques (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)).

Generally, antibody inhibitors comprise an antibody fragment that retains specificity for the antigen or epitope (e.g., TYK2, STAT3, phosphorylated STAT3, phosphorylated TYK2). The antibody inhibitor often targets a functional domain of the antigen, for example, the kinase domain of TYK2 or the dimerization domain of STAT3.

In some embodiments, the antibody inhibitor comprises a single chain antibody, e.g., an scFv. In some embodiments, the antibody inhibitor comprises an Fab region. In some embodiments, the antibody inhibitor is humanized.

2. Nucleic Acid Inhibitors

Modulators also include agents designed to reduce the level of mRNA encoding an neurodegeneration biomarker polypeptide (e.g., antisense molecules, ribozymes, DNAzymes, small inhibitory RNAs and the like) or the level of translation from an mRNA (e.g., translation blockers such as an antisense molecules that are complementary to translation start or other sequences on an mRNA molecule). In some embodiments, known methods are used to identify nucleic acid sequences that inhibit neurodegeneration biomarkers. Such inhibitors may include but are not limited to, siRNA oligonucleotides and antisense oligonucleotides. Inhibitor siRNA or antisense oligonucleotides can be used to specifically target TYK2 and STAT3 expression.

In some embodiments, RNA interference is used to generate small double-stranded RNA, small interference RNA (siRNA) or short hairpin RNA (shRNA)) inhibitors to affect the expression of TYK2 and STAT3 generally through cleaving and destroying its cognate RNA. Small interference RNA (siRNA or shRNA, used interchangeably) is typically 19-22 nt double-stranded RNA. siRNA can be obtained by chemical synthesis or by DNA-vector based RNAi technology. Using DNA vector based siRNA technology, a small DNA insert (about 70 bp) encoding a short hairpin RNA targeting the gene of interest is cloned into a commercially available vector. The insert-containing vector can be transfected into the cell, and expressing the short hairpin RNA. The hairpin RNA is rapidly processed by the cellular machinery into 19-22 nt double stranded RNA (siRNA). The siRNA is generally inserted into a suitable RNAi vector because siRNA made synthetically tends to be less stable and not as effective in transfection.

siRNA can be made using methods and algorithms such as those described by Wang et al. (2004) A Web-based Design Center for Vector-based siRNA and siRNA cassette Bioinformatics. (In press); Khvorova et al. (2003) Cell. 115(2):209-16; Harborth et al. (2003) Antisense Nucleic Acid Drug Dev.

13(2):83-105; Reynolds et al. (2004) *Nat Biotechnol.* 22:326-30; and Ui-Tei et al. (2004) *Nucleic Acids Res.* 32:936-48. Other tools for constructing siRNA sequences are web tools such as the siRNA Target Finder and Construct Builder available from GenScript, Oligo Design and Analysis Tools from Integrated DNA Technologies, or siDESIGN™ Center from Dharmacon, Inc. siRNA are suggested to be built using the ORF (open reading frame) as the target selecting region, preferably 50-100 nt downstream of the start codon.

3. Peptide and Small Molecule Inhibitors

The agents tested as modulators of the polypeptides or polynucleotides of the invention can be any small chemical compound, or a biological entity, such as a protein, sugar, nucleic acid or lipid. Test compounds often comprise small chemical molecules and peptides. Peptide inhibitors can be designed to mimic natural ligands or binding partners of the targeted molecule. In the context of the present invention, exemplary peptide inhibitors of STAT3 can be designed, e.g., from STAT3 dimerization partners. Exemplary peptide inhibitors of TYK2 can be designed, e.g., from natural substrates of TYK2.

Essentially any chemical compound can be used as a potential modulator in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one embodiment, high throughput screening methods involve providing a combinatorial chemical or peptide library containing a large number of potential therapeutic compounds (potential modulator compounds). Such "combinatorial chemical libraries" or "peptide libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks." For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

F. METHODS OF IDENTIFYING MODULATORS OF NEURODEGENERATION BIOMARKERS

The neurodegeneration biomarker polypeptides and polynucleotides for use in screening assays will generally be similar to the wild type STAT3 and TYK2 sequences and retain at least one biological activity of the protein. Optionally, the neurodegeneration biomarker polypeptide or polynucleotide used in activity assays will comprise a fragment of the full length sequence, such as a kinase domain, or transactivation domain. Either a polypeptide of the invention or a domain thereof can be covalently linked to a heterologous protein to create a chimeric protein used in the assays described herein. A polypeptide of the invention is active when it has an activity value, relative to the control, that is 110%, optionally 150%, 200%, 300%, 400%, 500%, or 1000-2000%.

Candidate modulators of neurodegeneration biomarker activity are tested using either recombinant or naturally occurring polypeptides. The protein can be isolated, expressed in a cell, expressed in a membrane derived from a cell, expressed in tissue or in an animal, either recombinant or naturally occurring. For example, tissue slices, dissociated cells, e.g., from tissues expressing polypeptides of the invention, transformed cells, or membranes can be used. Inhibition is tested using one of the in vitro or in vivo assays described herein.

Test compound binding to polypeptides of the invention, a domain, or chimeric protein can be tested in solution, in a bilayer membrane, attached to a solid phase, in a lipid monolayer, or in vesicles. Binding of a test compound can be tested using, e.g., changes in spectroscopic characteristics (e.g., fluorescence, absorbance, refractive index), hydrodynamic (e.g., shape), chromatographic, or solubility properties.

Samples or assays that are treated with a potential modulator (e.g., a "test compound") are compared to control samples without the test compound, to examine the extent of modulation. Control samples (untreated with candidate compounds are assigned a relative activity value of 100. Inhibition of the polypeptides of the invention is achieved when the activity value relative to the control is about 90%, optionally 50%, optionally 25-0%.

Screening assays for a compound that modulates the expression of neurodegeneration biomarker polynucleotides and polypeptides are also provided. Screening methods generally involve conducting cell-based assays in which test compounds are contacted with one or more cells expressing STAT3 or TYK2, and then detecting an increase or decrease in expression (either transcript or translation product). Assays can be performed with any cells that express a STAT3 or TYK2 polypeptide, e.g., a neuronal cell.

Expression can be detected in a number of different ways. As described above, the expression level of a neurodegeneration biomarker polynucleotide can be determined by probing the mRNA expressed in a cell with a probe that specifically hybridizes with a neurodegeneration biomarker transcript (or complementary nucleic acid derived therefrom). Alternatively, a neurodegeneration biomarker polypeptide can be detected using immunological methods, e.g., an assay in which a cell lysate is probed with antibodies that specifically bind to the polypeptide.

Reporter systems can also be used to identify modulators of neurodegeneration biomarker expression. A variety of different types of cells can be utilized in reporter assays. Cells that do not endogenously express a neurodegeneration biomarker polypeptide can be prokaryotic, but are preferably eukaryotic. The eukaryotic cells can be any of the cells typically utilized in generating cells that harbor recombinant nucleic acid constructs. Exemplary eukaryotic cells include, but are not limited to, HCN-1 (cortical neurons), 1321N1 (astrocytoma), 114 (glioma), IMR32, and PC12 cell lines.

Various controls can be conducted to ensure that an observed activity is authentic including running parallel reactions with cells that lack the reporter construct or by not contacting a cell harboring the reporter construct with test compound.

Activity can be assessed using a variety of in vitro and in vivo assays to determine functional, chemical, and physical effects. In the case of TYK2, these assays include monitoring, for example, catalytic phosphorylation of substrate. An exemplary kinase assay is provided in the examples. Alternatively, the ability of TYK2 to phosphorylate a substrate (e.g., STAT3) can be tested by incubating the substrate with TYK2 polypeptide in a buffer with $^{32}$P-γATP and measuring the amount of phosphorylated substrate.

Assays formatted for highthroughput use can also be used. For example, kinases catalyze the transfer of a gamma-phosphoryl group from ATP to an appropriate hydroxyl acceptor with the release of a proton. An assay based on the detection of this proton using an appropriately matched buffer/indicator system may therefore be used to detect activity (see, e.g., Chapman & Wong Bioorg Med Chem 10:551-5, 2002).

Alternatively, TYK2 and STAT3-mediated Caspase 3 cleavage and apoptosis can be used to assay for activity. In such assays, hallmarks of apoptosis, e.g., DNA fragmentation, cell viability are measured. Cell viability can be measured using an assay suitable for a high throughput screening format, such as a colorimetric or fluorescent viability assay. For example, an Alamar blue (AB) assay, incorporates a redox indicator that changes the color or fluorescence in response to metabolic activity. The Alamar blue fluoresces in the presence of living, but not dead, cells. Such an assay can be read in a microtiter plate or by flow cytometry. Colorimetric assays such as the MTT assay, which measures the reduction of MTT (3-(4,5-dimethyl) thiazol-2-yl-2,5-diphenyl tetrazolium bromide) to formazan, may also be used conveniently in a high throughput format to measure cell viability and proliferation.

Other assays that measure cell number may also be used. These include assays that measure intercalation of dyes into the DNA of a cell. The amount of intercalated dye is directly proportional to cell number. For example, cells can be stained with a dye such as Hoechst 33342, which intercalates in the DNA of vital cell, an cell number determined by measuring the amount of fluorescence. Cells may also be directly counted.

Alternatively, signaling events downstream of TYK2 and STAT3 can be used to assay activity. For example, expression of genes activated by STAT3 transactivation (e.g., iNOS, IRF-1) can be measured using techniques described herein. Alternatively, cleavage of caspase-3 can be detected, as described in the examples.

Compounds that are initially identified by any of the foregoing screening methods can be further tested to validate the apparent activity. Preferably such studies are conducted with suitable animal models. The basic format of such methods involves administering a lead compound identified during an initial screen to an animal that serves as an AD model for humans and then determining if AD is in fact modulated and/or ameliorated. The animal models utilized in validation studies generally are mammals of any kind. Specific examples of suitable animals include, but are not limited to, primates, mice, and rats. An exemplary animal model for AD is the APP/PS1 mouse.

G. EXAMPLES

1. Example 1

Figure 1:
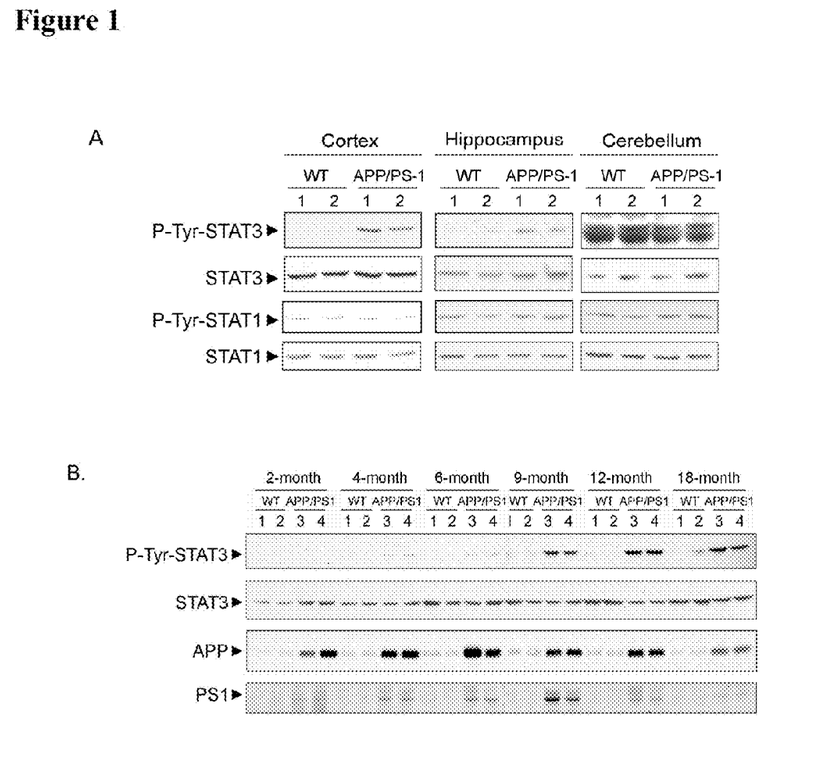
FIG. 1: Tyrosine phosphorylation of STAT3 is increased in cortex and hippocampus of transgenic AD model mice. A. Cortices, hippocampi and cerebelli from nine-month old APP/PS1 (APP695 with Swedish mutation KM670/671NL and PS1 ΔE9) double transgenic mice brains were lysed and subject to immunoblotting as indicated. B. Cortices from different stages of APP/PS1 transgenic mice brains were lysed and subjected to immunoblotting as indicated.

Phosphorylation of STAT3 at Tyr705 is Elevated in Brain Tissues of Alzheimer's Disease (AD) Model Mice To identify the signaling pathway(s) involved in AD pathology, the expression levels and functional status of various signaling molecules in AD mouse brain were screened. Lysates of distinct parts of brain tissues including cortices, hippocampi and cerebella were prepared from APP/PS1 transgenic mice [APP (Swe)/PS1 (ΔE9)] (9 months old), a well-characterized AD mouse model. Tyrosine phosphorylation of STAT3 was found to be consistently elevated in the cortex of the AD mouse brain (FIG. 1A). These findings suggest a link between elevated pTyr-STAT3 levels and AD pathology.

Increased tyrosine phosphorylation of STAT3 is detected in the cortex of AD mice from the age of 4 months up to 18 months (FIG. 1B). These AD mice have been reported to develop β-amyloid (Aβ) deposits, the main constituent of senile plaques in AD brains, at ~6-7 months of age, suggesting that tyrosine phosphorylation of STAT3 occurs prior to the formation of senile plaques.

While tyrosine phosphorylation of STAT3 is barely detected in the cortex of wild-type mice, a significant increase in tyrosine-phosphorylated STAT3 was observed in the cortex of APP/PS1 mice. By immunostaining, we found that the active (tyrosine-phosphorylated) STAT3 co-localizes with NeuN-positive neurons (>80%) but not with the GFAP-positive glial cells, further suggesting that STAT3 activation occurs mainly in the neurons of AD mouse brain. Moreover, tyrosine phosphorylation of STAT3 was found to occur in similar regions to that of senile plaques (indicated by Aβ staining) in the AD mouse brain.

2. Example 2

Aβ Induces Tyrosine Phosphorylation of STAT3 in Cortical Neurons

Figure 2:
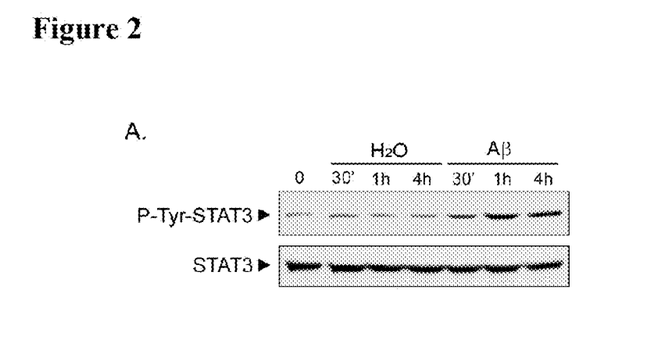
FIG. 2: Tyrosine phosphorylation of STAT3 is increased in cultured cortical neurons stimulated with Aβ25-35. Primary cortical neurons at 7 DIV were treated with Aβ25-35 (40 μM; $H_2O$ served as solvent control) for various times as indicated. Cell lysates were collected and subjected to immunoblotting using P-Tyr STAT3 and total STAT3 antibodies.

Cultured rat cortical neurons were used as a cell culture model to investigate the role of STAT3 tyrosine phosphorylation in AD. The cortical neurons (7 DIV) were treated with Aβ peptide 25-35. A significant increase in tyrosine phosphorylation of STAT3 was observed and the phosphorylation was sustained for all 4 hrs of Aβ treatment (FIG. 2). Immunostaining showed that tyrosine phosphorylation of STAT3 induced by Aβ treatment was concentrated in the β-tubulin III-positive neurons.

3. Example 3

Figure 3:
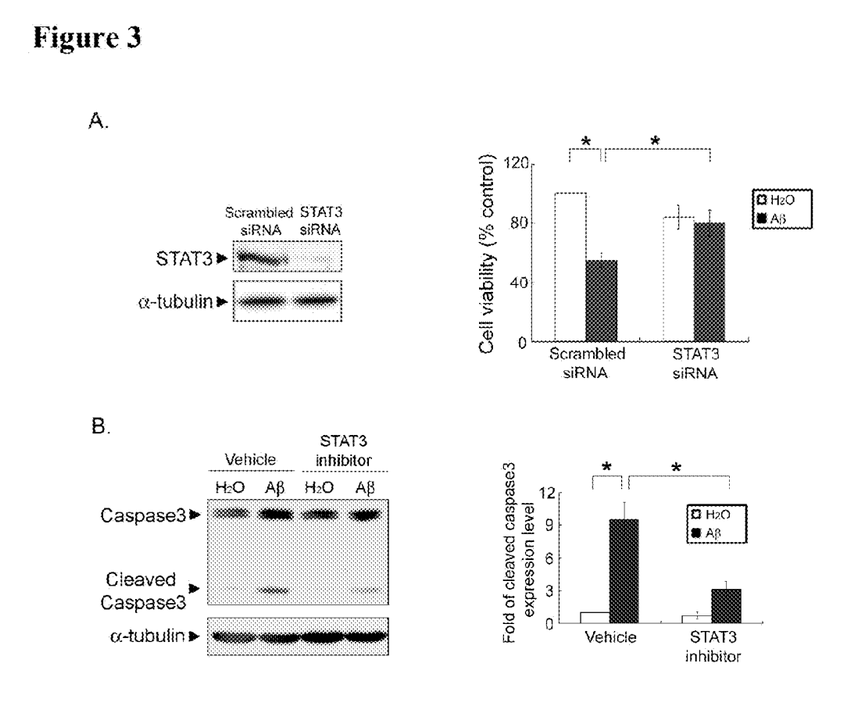
Figure 4:
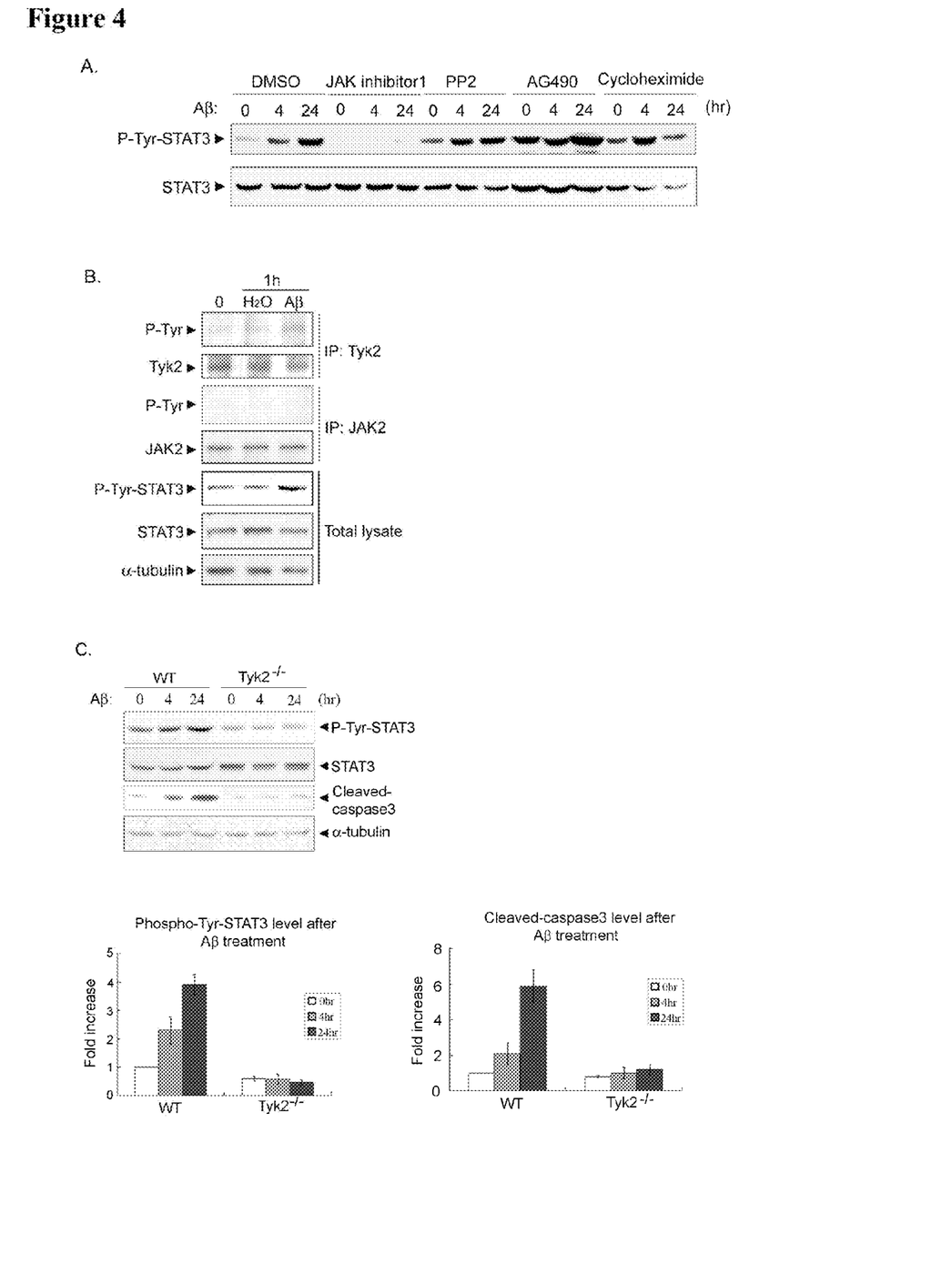

Knock-Down of STAT3 or Inhibition of STAT3 Activity Protect Neuronal Cells from Aβ-Induced Apoptosis To investigate the role of STAT3 in neuronal cell death in AD, STAT3 expression in PC12 cells was knocked down using STAT3 siRNA. Approximately 80% of STAT3 protein was knocked down (FIG. 3A). After undergoing differentiation (induced by NGF) for 4 days, the cells were treated with Aβ peptide. Knock-down of STAT3 reduced Aβ-induced cell death (FIG. 4A). Furthermore, inhibiting STAT3 activation by treating the cells with a specific STAT3 inhibitor reduced the levels of Aβ-induced cleaved caspase-3 (FIG. 3B), which indicates the extent of neuronal cell apoptosis. Caspase-3 is an intracellular cysteine protease involved in neuronal cell apoptosis. It is activated as part of the apoptotic response to cellular injury. Taken together, these findings suggest that STAT3 activity plays a key role in Aβ peptide-induced neuronal cell death.

4. Example 4

Tyk2 Mediates Aβ-Induced Tyrosine Phosphorylation of STAT3 and is Required for Aβ-Induced Neuronal Apoptosis Since Aβ induced tyrosine phosphorylation of STAT3, the next aim was to identify the upstream regulators of STAT3. Cortical neurons were pre-treated with different inhibitors prior to iv treatment. JAK inhibitor 1, which has a potent inhibitory effect on various tyrosine kinases up-stream of STAT3 including JAK1, JAK2, JAK3 and Tyk2, completely inhibited Aβ-induced tyrosine phosphorylation of STAT3 (FIG. 4A). However, a JAK2 inhibitor, AG490, did not exhibit similar inhibitory effects as that of JAK inhibitor 1. These findings suggested that Aβ-induced STAT3 phosphorylation is mediated via JAK family members other than JAK2. Additionally, neither the Src kinase inhibitor PP2 nor the protein synthesis inhibitor cycloheximide affected Aβ-induced STAT3 phosphorylation, indicating that Aβ-induced phosphorylation of STAT3 is: (i) not via the Src pathway; and (ii) does not require protein synthesis. Cortical neurons were treated with Aβ peptide for 1 hr. Endogenous Tyk2 or JAK2 were immunoprecipitated by specific antibodies, and the precipitates were detected by monoclonal phospho-tyrosine antibody, 4G10. In contrast with JAK2, the Tyk2 tyrosine phosphorylation could be detected in Aβ-treated cells (FIG. 4B).

The involvement of Tyk2 in Aβ-induced neuronal apoptosis was then examined. Primary cortical neuronal cultures were prepared from Tyk2$^{-/-}$ mice. In control neurons, treatment with Aβ peptide resulted in tyrosine phosphorylation of STAT3 at Tyr705. However, this specific phosphorylation was attenuated in Tyk2$^{-/-}$ neurons (FIG. 4C). In addition, caspase-3 activation and neuronal apoptosis, which are induced by Aβ, was also attenuated in Tyk2$^{-/-}$ neurons. Taken together, Tyk2 is required for Aβ-induced STAT3 phosphorylation and mediates Aβ-induced caspase-3 cleavage and neuronal cell death.

5. Example 5

Aβ Treatment in Cortical Neurons Induces iNOS Gene Expression

Figure 5:
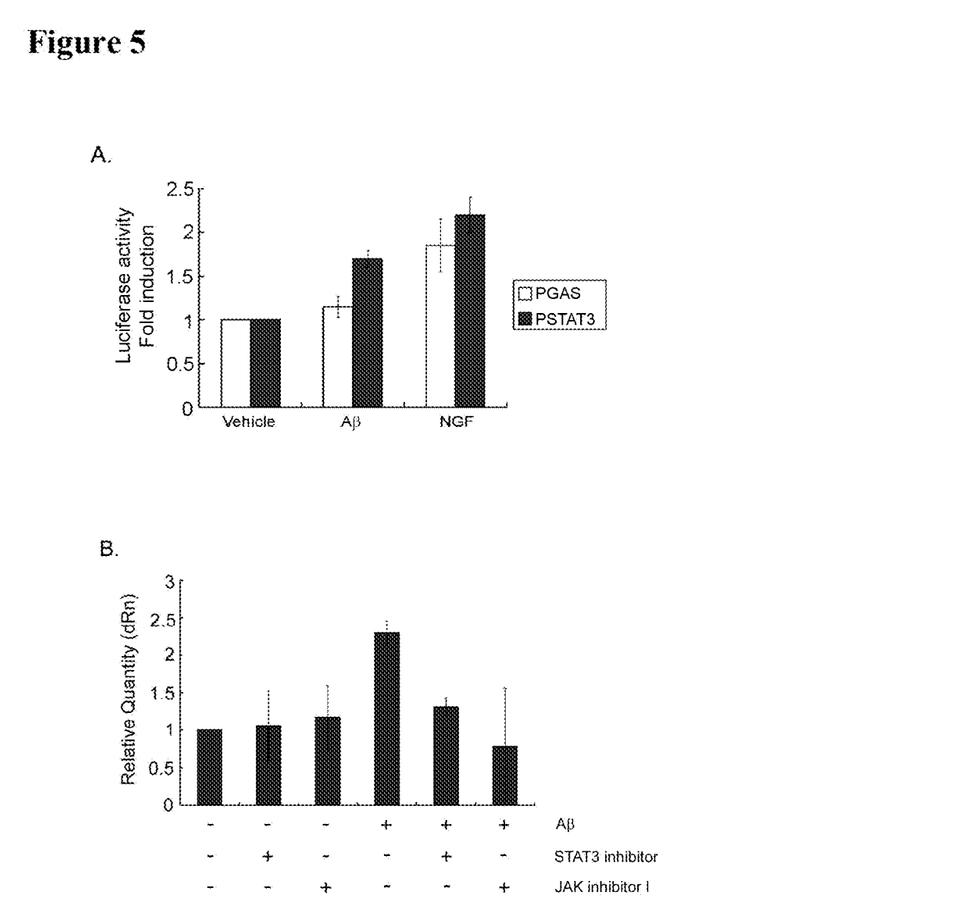

To further characterize if Aβ peptide effects STAT3 transcriptional activity, PC12 cells were transfected with a luciferase construct linked to the STAT3-response enhancer element (pSTAT3-Luc). The luciferase construct linked to the STAT1-response enhancer element (pGAS-Luc) was used as a control. Consistent with the previous report, NGF treatment induced the promoter activity of both STAT3 and STAT1, but Aβ peptide only induced the STAT3 promoter activity (FIG. 5A).

Primary cortical neurons were treated with Aβ peptide for 6 hr. Inducible nitric oxide synthase (iNOS) mRNA level was examined by real-time PCR. iNOS is one of the three types of nitric oxide synthase (NOS) in mammals that are responsible for the production of the gaseous signaling molecule, nitric oxide (NO). iNOS plays an important role in inflammation and pathogen-induced immune response. NO is generated by iNOS following exposure to certain cytokines, such as interferon-γ (IFN-γ), which signals through the JAK family and STAT proteins. Activated STATs dimerize and translocate to the nucleus where they increase expression of transcription factors, e.g., IRF-1, that, in turn binds to specific DNA elements of the iNOS gene promoter region to increase iNOS gene expression.

After Aβ peptide treatment, the iNOS gene expression level increased. Interestingly, this increase in iNOS gene expression could be blocked by the pretreatment of STAT3 inhibitor or JAK inhibitor 1, indicating that JAK-STAT pathway is necessary for Aβ-induced upregulation of iNOS gene expression (FIG. 5B).

6. Example 6

STAT3 Tyrosine Phosphorylation is Visible in AD Brain Slices

Figure 6:
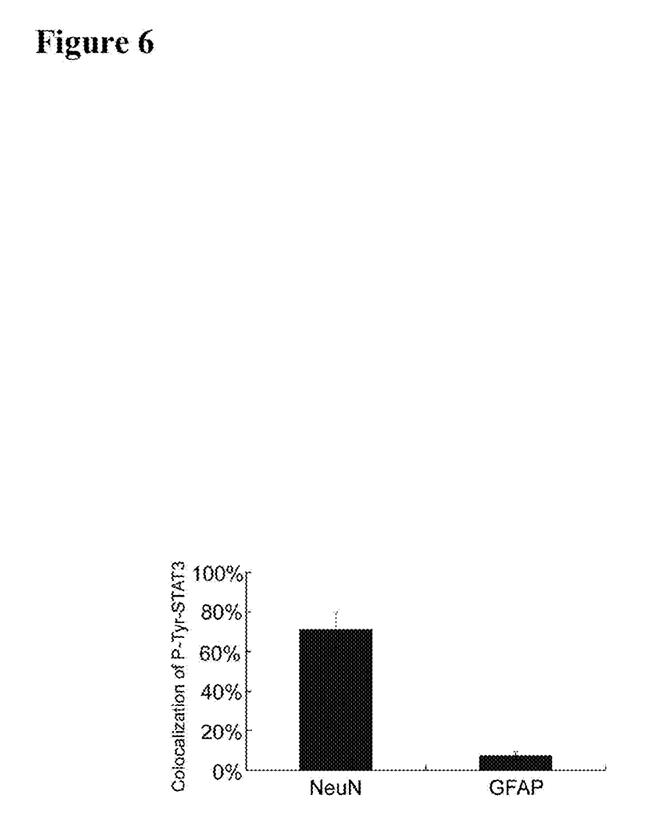
FIG. 6: Tyrosine phosphorylation of STAT3 increases in hippocampus of Alzheimer's disease patients. Paraffin sections of AD patient brain were stained using P-Tyr STAT3 antibody and neuronal-specific marker, NeuN or glial-specific marker GFAP. Quantification analysis of P-Tyr STAT3 staining indicated co-localization with NeuN and GFAP.

To determine whether STAT3 tyrosine phosphorylation is observed in the brains of AD patients, hippocampus brain slices from 4 AD patients were stained. All 4 patients exhibited a similar staining profile. Tyrosine phosphorylation of STAT3 was clearly observed in AD brain sections. By immunostaining, we also found that the active STAT3 co-localizes with NeuN-positive neurons (around 70%) but not with the GFAP-positive glial cells (around 7%), which is consistent with the result from APP/PS1 transgenic mice brain slices (FIG. 6).

7. Methods

Preparation of Brain Extracts, Cell Extracts, and Western Blots: Four Brain Parts including cortex, hippocampus, cerebellum and striatum were dissected from transgenic mice of various stages (from 2 months to 18 months) and kept on dry ice. Frozen brain tissues were homogenized in homogenizing buffer (25 mM Tris-HCl, pH 7.4, 150 mM NaCl, 1 mM EDTA, pH 7.4, 50 mM NaF) with various protease inhibitors. The supernatant was kept for Western Blotting and the pellets were reextracted using RIPA lysis buffer (150 mM NaCl, 1% (v/v) Nonidet P-40, 0.5% deoxycholic acid, 0.1% (w/v) SDS) containing various protease inhibitors (2 µg/ml aprotinin, 1 mM phenylmethylsulfonyl fluoride, 5 mM benzamidine, 1 mM sodium orthovanadate (NaOV), and 10 µg/ml soybean trypsin inhibitor). Primary cultured cortical neurons or PC12 cells were harvested and lysed in RIPA lysis buffer containing protease inhibitors.

Immunohistochemical analysis: Paraffin brain slices were boiled in 1 mM EDTA buffer (pH 8.0) for 5 min for antigen retrieval. The DAB or AEC staining were performed following the manufacturer's instruction. For the fluorescence immunostaining, brain sections were blocked with 4% goat serum in PBS containing 0.4% Triton X-100 at room temperature for 20 min. The sections were incubated with primary antibody (anti-NeuN; 1:200) and anti-phospho-STAT3 (Tyr705) (1:100) at 4° C. overnight, followed by Alexa Fluor 488-conjugated anti-mouse and Alexa Fluor 568-conjugated anti-rabbit IgG (Invitrogen, 1:1000) for 1 h at room temperature. The slices were then washed and mounted with anti-fade reagent (Invitrogen) and analyzed under Olympus confocal microscope (Fluoview BX61, Olympus). Cultured cortical neurons were fixed with 4% paraformaldehyde at room temperature for 30 min, then blocked with 4% goat serum in PBS containing 0.4% Triton X-100 for 20 min at room temperature. Immunocytochemical analysis was performed using anti-NeuN monoclonal antibody (1:500) and P-Tyr STAT3 polyclonal antibody (1:200) at 4° C. overnight. The cells were then labeled with Alexa Fluor 488 or Alexa Fluor 568-conjugated anti-mouse or anti-rabbit IgG (Invitrogen, 1:1000) at room temperature for 1 h. Neurons were then mounted with anti-Fade reagent (Invitrogen) and analyzed under Olympus confocal microscope (Fluoview BX61, Olympus).

Cell viability: Cell viability was quantified by its ability to reduce tetrazolium salt 3-(4,5-dimethylthiazol-2-yl)-2,5-diphenyl tetrasodium bromide (MTT) to a coloured formazan products (Cell proliferation kit I, Roche) according to the manufacturer's instruction. Briefly, MIT reagent (5 mg/ml in DPBS) was added to the cells (1/10 volume of medium). Cells were incubated at 37° C. for 4 hr. MTT Solubilization buffer (0.01M HCl, 10% SDS) of 2-fold volume was added to the cells, followed by an incubation in the dark at 37° C. for 24 hr. The absorbance was measured at 570 nm using a microplate reader (EYNEX REVELATION 4.22, MRC TC REVELATION DYNEX TECHNOLOGIES). MTT is taken only into viable cells. Cell viability was presented as a percentage of the absorbance of Aβ-treated cells relative to that of control culture.

Caspase-3 activity assay: Activity of caspase-3 was measured using CaspACE™ Assay System, Fluorometric kit (Promega). Briefly, the cells were lysed and the activity of caspase-3 in cell extracts was determined by fluorometric assay. The fluorescence emission of the AMC, resulting from a caspase-3-specific cleavage of the substrate peptide DEVD labeled with fluorochrome AMC, was measured using SpectraMaxGemini with an excitation wavelength at 360 nm and emission wavelength at 460 nm. Protein assay was performed as the normalization control.

Quantitative RT-PCR: Total RNA was isolated from Aβ-treated cortical neurons using RNeasy mini kit (Qiagen) according to the manufacturer's instruction. First strand cDNA was synthesized using random hexamers (Roche). Quantitative PCR was performed with specific primers targeting specific genes using Bio-Rad MX3000P real-time PCR system.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for identifying a compound that modulates a neurodegenerative disorder, the method comprising the steps of:
   (i) contacting a neuronal cell with a compound;
   (ii) determining the functional effect of the compound on STAT3,
   wherein the functional effect of the compound on STAT3 comprises increasing or decreasing phosphorylation of STAT3 at tyrosine 705, and
   (iii) identifying the compound as a compound that modulates a neurodegenerative disorder when the functional effect is detected.

2. The method of claim 1, wherein the neurodegenerative disorder is characterized by deposits of amyloid peptides in the brain.

3. The method of claim 1, wherein the neurodegenerative disorder is selected from the group consisting of: Alzheimer's Disease (AD), Parkinson's disease, Dentatorubro-pallidoluysian Atrophy (DRPLA), Neuronal Intranuclear Hyaline Inclusion Disease (NIHID), dementia with Lewy bodies, Down's Syndrome, Hallervorden-Spatz disease, prion diseases, argyrophilic grain dementia, cortocobasal degeneration, dementia pugilistica, diffuse neurofibrillary tangles, Gerstmann-Straussler-Scheinker disease, Hallervorden-Spatz disease, Jakob-Creutzfeldt disease, Niemann-Pick disease type 3, progressive supranuclear palsy, subacute sclerosing panencephalitis, Spinocerebellar Ataxias, Huntington's disease, Pick's disease, and dentatorubral-pallidoluysian atrophy.

4. The method of claim 1, wherein the functional effect is determined in vitro.

5. The method of claim 1, wherein the functional effect is determined in the neuronal cell.

6. The method of claim 1, wherein the neuronal cell in step (1) is further contacted with an agent that induces STAT3 phosphorylation at tyrosine 705.

7. The method of claim 6, wherein the agent is a β-amyloid peptide.

8. The method of claim 1, wherein the compound is an antibody or antibody fragment specific for STAT3 or TYK2.

9. The method of claim 1, wherein the compound is a peptide inhibitor specific for STAT3 or TYK2.

10. The method of claim 1, wherein the compound is a small organic molecule.

11. The method of claim 1, wherein the functional effect of the compound on STAT3 comprises inhibiting or decreasing phosphorylation of STAT3 on tyrosine 705.

* * * * *